United States Patent [19]
Jackson

[11] Patent Number: 6,045,526
[45] Date of Patent: Apr. 4, 2000

[54] INSERTION DEVICE WITH LASER ENGRAVED FINGER GRIP AND METHOD OF MAKING SAME

[75] Inventor: Dane R. Jackson, Bloomingdale, N.J.

[73] Assignee: Playtex Products, Inc., Westport, Conn.

[21] Appl. No.: 09/245,451

[22] Filed: Feb. 5, 1999

[51] Int. Cl.$^7$ .................................................. A61F 13/00
[52] U.S. Cl. .............................................. 604/15; 604/60
[58] Field of Search ...................... 604/11–18, 285–288, 604/904, 36, 38, 57, 59, 60, 311

[56] References Cited

U.S. PATENT DOCUMENTS

| | | | |
|---|---|---|---|
| 2,489,502 | 11/1949 | Ruth | 604/15 |
| 2,587,717 | 3/1952 | Fourness | 604/15 |
| 3,575,169 | 4/1971 | Voss | 604/15 |
| 3,628,533 | 2/1971 | Loyer | 604/15 |
| 3,645,263 | 2/1972 | Bates | 604/15 |
| 4,536,178 | 8/1985 | Lichstein et al. | 604/15 |
| 4,758,705 | 7/1988 | Hertzel et al. | |
| 5,290,501 | 3/1994 | Klesius | 604/14 |
| 5,322,988 | 6/1994 | Russell et al. | |
| 5,346,468 | 9/1994 | Campion et al. | |
| 5,395,308 | 3/1995 | Fox et al. | 604/15 |
| 5,420,575 | 5/1995 | Cheraso et al. | |
| 5,558,631 | 9/1996 | Campion et al. | |
| 5,709,652 | 1/1998 | Hagerty | 604/15 |

*Primary Examiner*—John G. Weiss
*Assistant Examiner*—Dennis Ruhl
*Attorney, Agent, or Firm*—Ohlandt, Greeley, Ruggiero & Perle, LLP

[57] ABSTRACT

An applicator is provided that has a textured finger grip. The textured finger grip is formed by exposing the applicator barrel to a beam of a laser to form deformations in the applicator barrel surface. The textured properties of the laser engraved finger grip of the present invention are enhanced when protuberances are superimposed on laser engraved areas by conventional embossing techniques. In addition, it is disclosed that effects of conventional embossing techniques are improved by embossing over areas that have been previously been exposed to a beam of a laser. Processes for manufacturing applicator barrels having the aforementioned textured fingergrips are also provided.

19 Claims, 3 Drawing Sheets

INSERTION DEVICE WITH LASER ENGRAVED FINGER GRIP AND METHOD OF MAKING SAME

BACKGROUND OF THE INVENTION

1. Field of the Invention

This invention relates to an insertion device. More specifically, this invention relates to an insertion device, such as a tampon applicator, having a textured finger grip formed by laser engraving.

An insertion device or applicator normally has two components, namely a barrel and a plunger. The material to be expelled, such as a tampon or tampon pledget, is usually positioned in the barrel. The barrel has a first end for ejection of the tampon, and a second end for receipt of the plunger that is adapted to telescopically slide in the barrel. To use the applicator, the consumer will position the ejection end appropriately, grasp the barrel and move the plunger in the barrel toward the first end of the barrel. Due to the manipulation required, a barrel must be easy to grip and hold so that undue pressure is not applied to the barrel or plunger.

In recent years, tampon applicators, especially the barrels, have coated exterior surfaces to minimize any possible discomfort experienced by the consumer during the insertion of the applicator. However, the coated exterior surface has ironically resulted in the barrel becoming more difficult to grip without undue pressure.

Thus, there is a need for an applicator, specifically an applicator barrel, that has a smooth exterior to minimize any discomfort to the user upon insertion, yet has a textured area for a greater degree of control or grippability. In addition, such a textured area must be economical to manufacture.

2. Description of the Prior Art

U.S. Pat. Nos. 5,346,468 and 5,558,631 to Campion et al. each disclose a tampon applicator that is formed from a paper laminate and that has an outer polymer coating. The outer polymer coating is capable of delaminating as a self-supporting layer. The Campion patent discloses that the tampon applicator may have a gripping area comprised of raised formations and/or depressions formed by embossing. However, the texture gripping area of the Campion tampon applicator is formed only by use of prior art embossment techniques.

Accordingly, there is a need for an insertion device with a finger grip area that has a greater definition of texture to facilitate use of the insertion device. There is also a need to provide a method for manufacturing such an insertion device in an efficient, cost effective manner.

BRIEF SUMMARY OF THE INVENTION

It is an object of the present invention to provide an insertion device having a textured finger grip that is formed by etching or engraving the surface of the barrel with a beam of a laser.

It is another object of the present invention to provide such an insertion device having an aesthetically pleasing, textured finger grip that includes one or more deformations or depressions formed by a beam of a laser and one or more protuberances formed by conventional embossing techniques.

It is still another object of the present invention to provide such an insertion device having a textured finger grip in which the areas of laser-formed depressions or deformations are interspersed with protuberances.

It is a yet another object of the present invention to provide such an insertion device having a finger grip in which the texture is provided by protuberances formed by embossing in areas previously weakened by depressions previously formed by a beam of laser.

It is a further object of the present invention to provide a method of manufacturing such an insertion device.

It is still a further object of the present invention to provide such a method of manufacturing a tampon applicator barrel having a textured finger grip that is formed by etching or engraving the surface of the barrel with a beam of a laser.

It is yet a further object of the present invention to provide such a method of manufacturing a tampon applicator having a textured finger grip that is formed by areas etched by a beam of laser interspersed with areas that are embossed.

It is an additional object of the present invention to provide a method of manufacturing such a tampon applicator having a textured finger grip in which the texture is provided by areas formed by embossment that are superimposed over areas of laser etching or engraving.

To accomplish these and other objects, the present invention is, in brief summary, an insertion device having a barrel with a textured finger grip formed by exposure of the barrel to a beam of a laser.

DETAILED DESCRIPTION OF THE INVENTION

Figure 1:
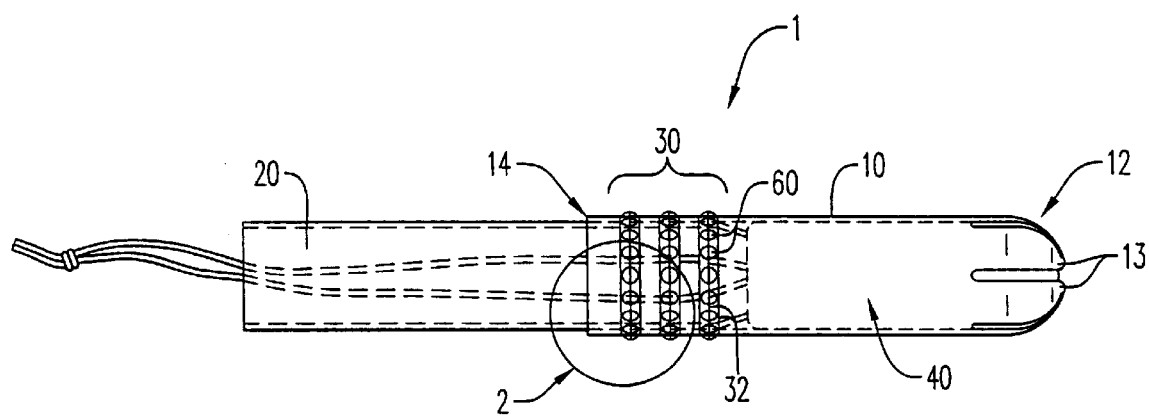
FIG. 1 is a side view of one embodiment of the present invention in which the areas of embossments are superimposed over areas of laser engraving.

Referring to the drawings and, in particular, FIG. 1, there is provided a first preferred embodiment of the present tampon applicator generally represented by reference numeral 1. The tampon applicator 1 has a barrel 10 and a plunger 20. The barrel 10 is adapted to receive a tampon or tampon pledget 40 therein. The barrel 10 has an expulsion or ejection end 12, and an opposite rear end 14. The expulsion end 12 preferably has one or more tips or petals 13 that form a dome-shape. Alternatively, expulsion end 12 can be a series of pleats (not shown). As a further alternative, expulsion end 12 can be simply an edge.

The tampon applicator 1 and, especially barrel 10, can be made of paper, cardboard or a polymer-based resin. Although it is not required, it is preferred that barrel 10 be coated with an epoxy, nitrocellulose, cellophane or polymer-based resin. The more preferred coatings are nitrocellulose and polyester. Most preferably, barrel 10 is formed from paper or cardboard, and has an outer polyester film coat and an intermediate polyethylene layer between the paper and polyester layers.

The plunger 20 is telescopically and slidably movable in barrel 10. The plunger 20 can be connected to barrel 10 or they can be two separate components that are connected together, such as, for example, plunger 20 can be positioned in rear end 14 of barrel 10 prior to use.

The barrel 10 has an exterior surface 16. The exterior surface 16 has a finger grip or finger grip area 30 thereon. Preferably, the finger grip 30 is located proximate to rear end 14 of barrel 10.

In a preferred embodiment, the finger grip 30 is entirely formed by laser engraving or etching one or more grooves 32 in or on the exterior surface 16 of barrel 10. Laser engraving as used in the present invention means engraving or etching in a substrate a depression, deformation or groove by a beam of a laser. It is understood that the depression can be so extreme that a perforation is formed that transverses all layers of the barrel.

Each groove 32 preferably is formed in the exterior surface 16 of barrel 10 about the circumference of the barrel. As stated above, it is preferable that groove or series of grooves 32 be proximate rear end 14. The width and depth of each groove 32 may vary based on the substrate of the barrel, namely paper, cardboard or polymer resin, the coating on the exterior surface 16, the power of the laser and the laser beam transversing speed.

In a more preferred embodiment, finger grip 30 preferably also has, in combination with one or more grooves 32, one or more embossments or protuberances 60. Preferably, each protuberance 60 is formed by embossing, a technique known in the art. In a preferred embodiment, illustrated generally in FIGS. 1 and 2, in which there are protuberances in combination with the laser engraved grooves 32, each protuberance 60 preferably has a circular base about 0.045 to about 0.080 inches in diameter. Preferably, each protuberance has a height 62 greater than 0.009 inches.

The finger grip 30 is located on exterior surface of barrel 10. Preferably, finger grip 30 is located on the barrel 10 proximate to rear end 14. More preferably, finger grip 30 is formed on the third of the barrel 10 proximal to rear end 14.

Each groove 32, and thus the finger grip 30, of the present invention is formed by directing a moving laser beam across the exterior surface 16 onto the material from which the barrel 10 is made. The moving laser beam preferably has a diameter of 180μm and is preferably a 25 watt sealed carbon dioxide ($CO_2$) laser. The beam transversing speed is preferably about 15 inches/second. When the applicator blank is formed from paperboard, it is preferred that the laser beam has a wavelength of about 10.6 μm. Examples of devices that may be used to create the laser beam necessary to practice the present invention are stearable sealed carbon dioxide lasers. However, a preferred device to practice the present invention is a sealed $CO_2$ laser model # 48-2-28W that is available from Synrad of Mukilteo, Wash having a stearable marking head model # SH3-125C that is also available from Synrad. Higher-powered lasers can also be used if there is an appropriate increase in laser beam transversing speed.

The energy from the laser light vaporizes barrel 10 to create a depression that may include a perforation. As stated above, the depth of vaporization of barrel 10 will depend upon the following factors, namely the material of barrel 10 and the type of material coating and depth of coating on exterior surface 16, the power of the laser, and the laser beam transversing speed.

Figure 2:
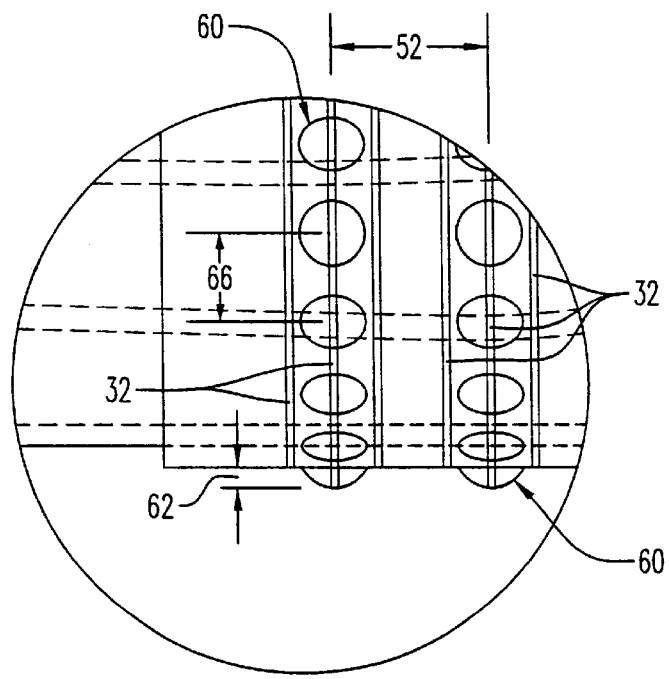
FIG. 2 is an enlarged view of a portion of the finger grip of the insertion device shown in FIG. 1.
Figure 3:
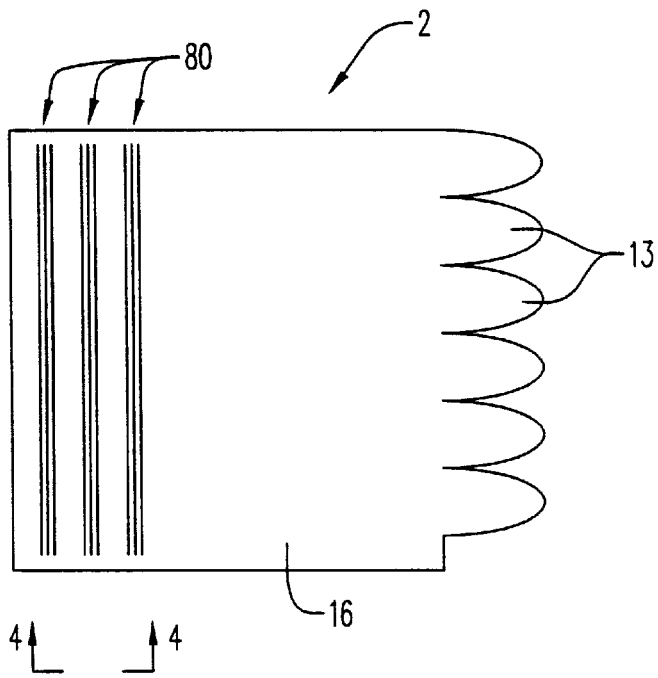
FIG. 3 is an elevational view of a flat applicator blank of a second embodiment of the present invention in which the laser engraved grooves are formed about what will be the circumference of the formed barrel of the insertion device.
Figure 4:
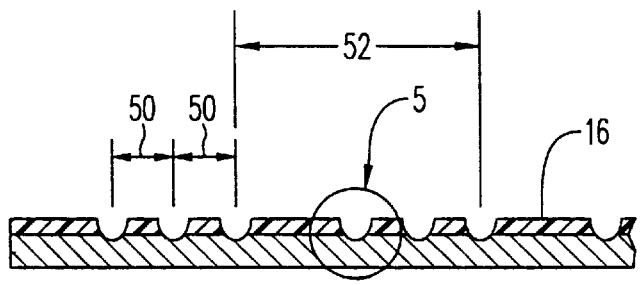
FIG. 4 is a partial cross-sectional view of the flat applicator blank of FIG. 3 take along line 4—4.
Figure 5:
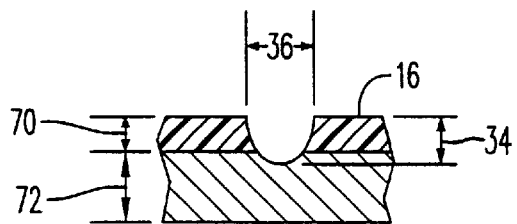
FIG. 5 is an enlarged view of a single laser engraved depression of FIG. 4.

Referring to the applicator blank generally represented by reference numeral 5 and illustrated in FIGS. 3, 4 and 5, a barrel 10 having a cardboard substrate 72 about 0.015 inches thick and a polyester coating or layer 70 about 0.0005 inches thick is formed. In order to form a preferred finger grip 30, the laser beam creates one groove 32 about 0.002 to about 0.005 inches deep 34 and about 0.010 to about 0.015 inches wide 36. In a preferred embodiment, grooves 32 are continuously formed about the circumference of barrel 10. However, grooves 32 can be formed discontinuously about the circumference of exterior surface 16 of barrel 10. In addition, each groove 32 can be a pattern of geometric shapes positioned about the circumference of exteriors surface 16 of barrel 10. In a more preferred embodiment illustrated generally in FIGS. 3 and 4, there are three sets 80 of grooves 32, with each set 80 having three grooves. Each groove 32 in a set is about 0.063 inches +/−0.025 inches apart 50 centerline from centerline. Also, the corresponding groove 32 in one set is spaced apart 52 from the corresponding groove 32 in the adjacent set by about 0.25 inches +/−0.08 inches. In one preferred embodiment, discussed above and illustrated generally in FIGS. 1 and 2, the center groove of each set of three grooves has protuberances 60 superimposed thereon at regular intervals. As stated above, it is preferred that protuberances 60 are formed by embossing. It is also preferred that the protuberances are spaced apart by intervals 66 of about 0.11 inches. More preferably, the protuberances are spaced along the circumference of the applicator barrel 10 by intervals 66 of about 0.11 inches.

In one more preferred embodiment, illustrated generally in FIGS. 1 and 2, in which there is three sets with each set consisting of a row of embossments or protuberances 60 flanked on either side by a row of laser engraved grooves, the protuberances 60 are about 0.11 inches apart centerline to centerline in a circumferential row. Also, the distance 68 between corresponding rows of protuberances 60 in adjacent sets is about 0.25 inches +/−0.08 inches.

As stated above, the laser beam may also be used to create perforations, as well as depressions. The laser beam and/or applicator 1 may be manipulated with respect to each other so that aesthetic patterns are formed on applicator barrel 10. For example, it is possible to form textured finger grip 30 to include grooves, spirals, depressions, perforations, trademarks, text and combinations thereof.

When an applicator, especially a paper or cardboard applicator, is provided with a laser engraved or etched finger grip, finger grip 30 may also be embossed by conventional embossment techniques. In a preferred method, embossing creates a raised formation or protuberance 60 in finger grip 30. Such protuberances 60 of barrel 10 may be interspersed with or superimposed on laser engraved grooves 32 of the finger grip. When the embossing process is applied to non-laser engraved areas, the resultant protuberance 60 will enhance the height of the texture of grooves or depressions 32 created by laser engraving. When the embossing process is superimposed on grooves or depressions 32 that were created by the laser engraving, the resulting embossment will have more definition than the embossment formed by conventional embossing techniques. This improved embossment is especially noted when barrel 10 is formed from cardboard and has an outer polymer film coating. The enhanced embossment is due to the vaporization of the outer polymer coating and, usually, portions of the underlying cardboard applicator by the laser engraving process. The loss of the reinforcing layers leaves barrel 10 more malleable. Thus, any embossments that are created, whether rings or protuberances, will have more definition in structure than conventional embossment to non-laser engraved areas.

Figure 6:
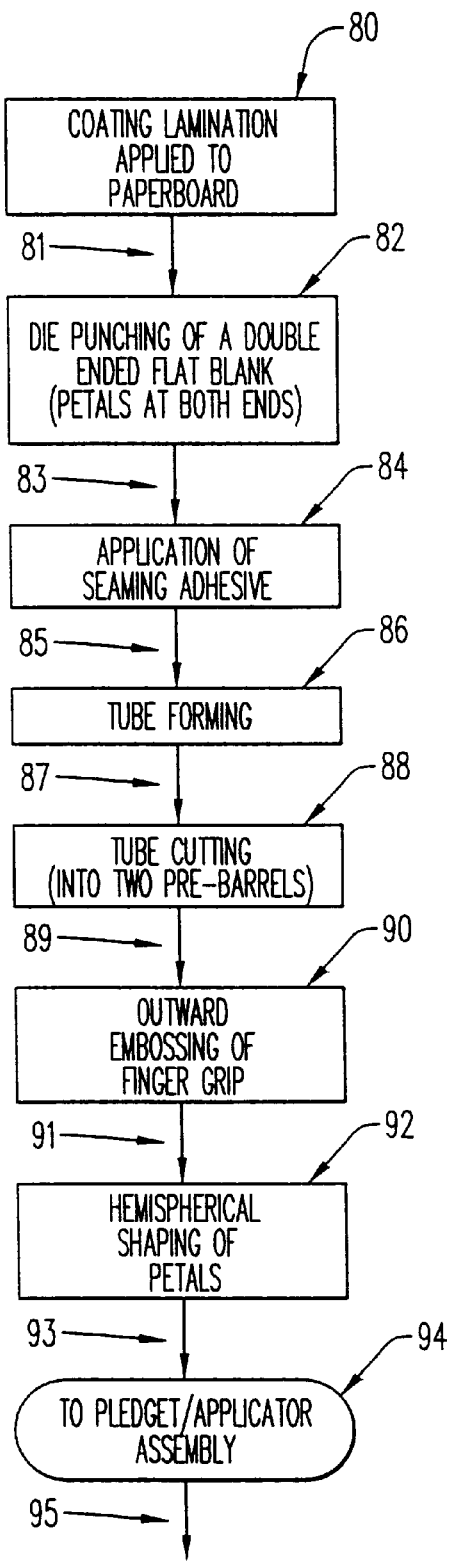
FIG. 6 is a flow chart that describes the process of manufacturing an applicator of the present invention.

A process of manufacturing a conventional cardboard or paperboard applicator that may be modified to incorporate the laser engraving process of the present invention is illustrated in FIG. 6 and proceeds as follows. First, in a preferred process of practicing the present invention, a coating of lamination is applied to paperboard 80. Second, the laminated paperboard is die punched to create a flat applicator blank 82. The die punched applicator blank may be double ended and/or have "petals". Third, seaming adhesive is applied to the die punched applicator blank 84. Fourth, the applicator blank is then rolled into a tube 86 and held in the tube configuration by the seaming adhesive. If a double-ended applicator blank was formed in the flat applicator blank, then the formed tube may be cut by conventional means to create two barrels 88. Fifth, outward embossing of the barrel, if desired, is performed at step five, 90. If "petal ends" were created, then the "petals" may be shaped into a hemi-spherical/dome-like shape 92. Optionally, at a point after step five 90, pledget 40 is assembled 94 in applicator barrel 10 and/or with plunger 20 connected to rear end 14 at 94 using conventional means.

Depending on whether certain optional steps, described above, are used, the laser engraving process of the applicator barrel to form the finger grip of the present invention may occur at the following points in the above-described process: after step one 80, at 81, after step two 82, at 83, after step three 84, at 85, after step four 86, at 87 or 89, or after step five 90, at 91 or 93. It is more preferred that the laser engraving process is at 81, 83 or 91. It is most preferred that that laser engraving process is conducted at 81 or 83.

Alternatively, the step of laser engraving applicator barrel 10 may be accomplished after either pledget or plunger 20 is inserted into the barrel 95. However, this is the least preferred method of producing an applicator of the present invention since handling at this point is more difficult. For example, the heat created during the process of laser engraving may negatively affect pledget 40 and, perhaps, plunger 20.

Various modifications and alterations to the present invention may be appreciated based on a review of this disclosure. These changes and additions are intended to be within the scope and the spirit of this invention as defined by the following claims.

I claim:

1. An applicator barrel comprising:

an outer surface having a textured area, wherein said textured area has at least one deformation formed by superimposing a protrusion on a deformation, said deformation provided by exposing said outer surface to a beam of a laser.

2. The applicator barrel of claim 1, wherein said at least one deformation is a depression.

3. The applicator barrel of claim 2, wherein said depression forms a circumferential groove on said outer surface of the applicator barrel.

4. The applicator barrel of claim 3, comprising a plurality of said circumferential grooves.

5. The applicator barrel of claim 4, wherein said plurality of circumferential grooves form at least two or more distinct sets of rows about said outer of said barrel.

6. The applicator barrel of claim 5, further comprising a second plurality of protuberances that form two or more rows of protuberances interspersed with the two or more distinct sets of grooves.

7. The applicator barrel of claim 1, wherein said at least one protuberance is a plurality of protuberances.

8. The applicator barrel of claim 7, wherein said outer surface has an outer circumference, and wherein said plurality of protuberances are spaced approximately in an equidistant manner around the outer circumference.

9. The applicator barrel of claim 1, wherein the applicator barrel is made of a material selected from the group consisting of paper and cardboard, and wherein the applicator barrel has an exterior surface that is coated with a coating selected from the group consisting of epoxy, cellophane, nitrocellulose and a polymer-based resin.

10. The applicator barrel of claim 9, wherein the applicator barrel is made of a material selected from the group consisting of paper and cardboard, and wherein the coating is polyester.

11. The applicator barrel of claim 1, wherein said at least one protuberance is formed by embossing.

12. The applicator barrel of claim 1, wherein said at least one deformation perforates the applicator barrel.

13. The applicator barrel of claim 1, further comprises at least one protuberance that is not superimposed on said at least one deformation.

14. The applicator barrel of claim 1, further comprising a plurality of said deformations.

15. A process for forming a textured area on an outer surface of an applicator barrel, said process comprising the step of:

producing a deformation on said outer surface by exposing said outer surface to a beam of a laser, and embossing at least one protuberance, said protuberance superimposed upon said deformation.

16. The process of claim 15, further comprising forming at least one additional protuberance that is not superimposed on the deformation.

17. The process of claim 16, further comprising a plurality of non-superimposed protuberances.

18. The process of claim 15, wherein the step of producing a deformation produces a plurality of deformations, and the step of forming a protuberance forms a plurality of protuberances on each of said plurality of deformations.

19. An applicator barrel comprising:

an outer surface having a textured area, wherein said textured area has at least one deformation formed by exposing said outer surface to a beam of a laser, and at least one protuberance superimposed upon said deformation, said protuberance formed by embossing.

* * * * *